United States Patent [19]

Tanekawa et al.

[11] 4,303,680

[45] Dec. 1, 1981

[54] PRODUCTION OF YEAST EXTRACT CONTAINING FLAVORING

[75] Inventors: Tetsuo Tanekawa; Hiroshi Takashima, both of Kawasaki; Tomoyoshi Hachiya, Kunitachi, all of Japan

[73] Assignee: Ajinomoto Company, Incorporated, Tokyo, Japan

[21] Appl. No.: 109,083

[22] Filed: Jan. 2, 1980

[30] Foreign Application Priority Data

Jan. 5, 1979 [JP] Japan ................................ 54-798

[51] Int. Cl.$^3$ ......................... A23L 1/28; A23L 2/26; C12N 1/06; C12N 1/08
[52] U.S. Cl. ..................................... 426/60; 426/537; 435/89; 435/256; 435/259; 435/267; 435/270
[58] Field of Search ..................... 426/60, 656, 537; 435/89, 255, 256, 259, 267, 272, 270

[56] References Cited

U.S. PATENT DOCUMENTS

| | | | |
|---|---|---|---|
| 3,867,255 | 2/1975 | Newell et al. | 426/60 X |
| 3,991,215 | 11/1976 | Robbins | 426/60 |
| 4,066,793 | 1/1978 | Eguchi | 426/60 |

FOREIGN PATENT DOCUMENTS 45-937 6/1970 Japan .
933828 8/1963 United Kingdom .

OTHER PUBLICATIONS

Treatment of Yeast Cells and Protein, Food Technology Review, No. 45, 1977, pp. 138-143.

*Primary Examiner*—David M. Naff
*Attorney, Agent, or Firm*—Oblon, Fisher, Spivak, McClelland & Maier

[57] ABSTRACT

A yeast extract containing flavoring 5'-neucleotide and having an improved thickness or body in taste is produced by (1) autolyzing suspended yeast cells in the presence of a stimulator of autolysis at a constant pH ranging from 6.0 to 6.6, then (2) heating the autolyzed suspension at a temperature of 90°–110° C. for 1 to 3 hours thereby extracting intracellular ribonucleic acid; and thereafter performing the following steps in any order; (3) hydrolyzing the extracted ribonucleic acid with a 5'-phosphodiesterase and; (4) separating the resulting extract from the insoluble residue.

5 Claims, No Drawings

PRODUCTION OF YEAST EXTRACT CONTAINING FLAVORING

FIELD OF THE INVENTION

The present invention relates to a method for producing a yeast extract having excellent high quality and improved flavor. More particularly, it is concerned with a method for producing an yeast extract characterized as having a improved thickness or body in taste which comprises the steps of decomposing suspended yeast cells by autolysis under the condition in which a decomposition of intracellular RNA is suppressed as little as possible, extracting the RNA from the autolysed yeast cells by heating the autolysate suspension, and hydrolysing the extracted RNA with enzyme into 5'-nucleotides.

DESCRIPTION OF THE PRIOR ART

While the supply of beef extract or whale extract is limited, yeast extract can be easily prepared from baker's yeast and bear yeast in large quantities at a low price, and has been widely used as a component of various seasonings. According to a conventional method, yeast extracts can be prepared by autolysis, or by hydrolysis using enzymes, acid or alkali. Among these methods, autolysis is the most preferred method since the quality of the resulting yeast extract is excellent.

It has been known that the quality of the yeast extract, especially thickness or body in taste, can be improved by addition of disodium guanosine-5'-monophosphate (GMP) or disodium inosine-5'-monophosphate (IMP) which is known to be a flavoring ingredient of a shiitake mushroom or dried skipjack.

And it has been well known that a considerable amount of RNA is contained in yeast cells. But, unfortunately, a yeast extract containing a substantial amount of flavoring 5'-nucleotides such as GMP can not be obtained because the intracellular RNA of yeast cells is usually decomposed to non-flavoring low molecular substances such as nucleosides or bases during the autolysis process. And the amount of GMP, supposing GMP is formed during autolysis, to too little to improve the quality of a yeast extract. In fact, no flavouring 5'-nucleotide can be detected in commercial yeast extracts.

According to a conventional method, a yeast extract containing flavoring 5'-nucleotides is prepared by extracting an intracellular RNA from yeast cells by heating a suspension of yeast cells containing 5~15% NaCl, hydrolysing the extracted RNA with 5'-phosphodiesterase into 5'-nucleotides containing GMP, and adding the resulting flavoring 5'-nucleotides to an acid or enzyme-hydrolysed solution of residual yeast cells from which RNA is previously extracted.

However, this conventional method is not economical since an expensive enzyme has to be used, and in this process, enzyme contained inherently in yeast cells themselves which is capable of autolysing or hydrolysing the yeast cells is not utilized at all. Moreover, the quality itself of yeast extract is not good since it is not prepared by autolysis method.

Another common method for producing a yeast extract containing flavoring 5'-nucleotide is also known, which uses a special enzyme derived from a microorganism belonging to a ray fungus in order to produce flavoring 5'-nucleotides in the autolysis process.

But, this process can not be carried out practically since the safety of the enzyme and microorganism used for producing the enzyme are not legally approved.

SUMMARY OF THE INVENTION

It is, therefore, a principal object of the present invention to provide a new economical method for producing a yeast extract containing flavoring 5'-nucleotide, and having thickness or body in taste.

It has been found that 50~80% of an intracellular RNA remains not decomposed in autolysed yeast cells, while most of the protein in yeast cells is almost hydrolysed into its constituting amino acids and oligopeptides when autolysis of yeast cells is carried out at a constant pH ranging from 6.0 to 6.6, more preferably from 6.2 to 6.4; that the remaining intracellular RNA can be easily extracted from the autolysed yeast cells by only heating the autolysate solution without use of NaCl, and that a yeast extract containing flavoring 5'-nucleotide and having a thickness or body in taste can be prepared by hydrolysing the extracted RNA with 5'-phosphodiesterase or 5'-phosphodiesterase and an AMP deaminase, in order to produce a flavoring 5'-nucleotide such as GMP and IMP.

DESCRIPTION OF THE PREFERRED EMBODIMENTS

The method of the present invention comprises the steps of:
(1) autolysing yeast cells in the presence of a stimulator of autolysis at a constant pH ranging from 6.0 to 6.6, more preferably 6.2 to 6.4, and a temperature of 30° to 60° C. for 10 to 30 hours;
(2) heating the autolysed suspension of yeast cells at a temperature of 90° to 100° C. for 1.0 to 3.0 hours, to extract remaining RNA and thereafter performing the following steps in any convenient order;
(3) hydrolysing the extracted RNA with 5'-phosphodiesterase converting AMP into IMP with AMP deaminase if desired, and;
(4) separating resulting clear extract from the insoluble residue.

According to the present invention, any of a variety of eddible yeast may be employed. These include baker's yeast such as Saccharomyces cerevisiae CBS 1172, CBS 1234, beer yeast such as Saccharomyces cerevisiae CBS 1171, CBS 1230, and Saccharomyces uvarum CBS 1503, and Saccharomyces carlsbergensis IFO 2015, sake yeast such as Saccharomyces cerevisiae IFO 2165, IFO 2342, wine yeast such as Saccharomyces cerevisiae IAM 4274, and Pichia farinosa CBS 2004, CBS 2006.

The yeast strains identified in this specification by accession numbers preceded by CBS are freely available from the Centraalburear voor Schimmelkultures, Baarn, Netherland. Those identified by accession numbers preceded by IFO are available from the Institute for Fermentation, Osaka, Japan.

For use in the invention, yeast cells are prepared by an entirely conventional method using a culture medium containing carbon source such as glucose, sucrose, starch hydrolysate, molasses, organic acids, and alchohol.

Yeast cells obtained as residues from the brewing of beer, sake and wine are especially useful in the practice of the present invention, which may be used for autolysis without the actual isolation of the yeast cells.

Among these yeast cells, fresh yeast cells obtained by culturing baker's or beer yeast, especially Saccharomyces cerevisiae CBS 1171, or CBS 1172, under aerobic condition in a common nutrient culture medium is preferable since yeast extract obtained from fresh yeast cells has less of an unfavorable odor and taste than other yeast cells.

For autolysis, the quantity of yeast cells in the suspension is preferably 5 to 20% by weight relative to the weight on a dry basis.

Autolysis is usually performed in the presence of 1 to 5% stimulator of autolysis such as ethyl acetate at a constant pH ranging from 6.0 to 6.6 and a temperature 30° to 60° C., more preferably 6.2~6.4 at 45°~55° C., and it is usually carried out for 10 to 30 hours.

As autolysis proceeds, a pH of the suspension of yeast cells drops sharply, therefore, it is necessary to control the pH within the desirable range mentioned above by adding alkali to the suspension.

The method of the present invention is characterized first by performing an autolysis of yeast cells effectively under the specific condition where protein of yeast cells is hydrolysed effectively to its constituting amino acids and oligopeptides, while the decomposition or hydrolysis of intracellular RNA is supressed as less as possible, that is, by performing the autolysis at a constant pH ranging from 6.0 to 6.6

When the autolysis of the yeast cells is carried out at such a constant pH as mentioned above, although intracellular RNA is hydrolysed in part to non-flavoring low molecular ingredients, 50~80% of the RNA remains not decomposed in the autolysed yeast cells, and components other than RNA, such as protein, are effectively hydrolysed to their constituting amino acids and oligopeptides, and a yield of solid matter expressed by total extracted solid matter/yeast cells ratio in percentages reaches usually 40 to 65%.

The second characteristic of the present invention resides in step (2) of extracting the remaining RNA from the autolysed yeast cells by heating the autolysed yeast cells without use of NaCl.

Usually, it is necessary to use a fairly highly concentrated NaCl solution to extract RNA effectively from yeast cells since RNA can not be extracted without NaCl.

Compared with the common method, the remaining intracellular RNA in the autolysed yeast cells can be easily extracted by only heating the autolyzed suspension at a temperature of 90° to 100° C. for 1 to 3 hours without use of NaCl.

Both the yield of solid matter and the quantity of extracted RNA i.e., the quantity of flavoring 5-nucleotide in resulting yeast extract are largely influenced by the pH at which autolysis is conducted. As shown in table 1, when autolysis is performed at a pH below 6.0 (5.5~5.8), although the yield of solid matter is more than 60% and this value is relatively high, the GMP-forming ratio (5'-GMP/dried yeast extracted ratio in percentages) is as low as zero to 0.17%. It seems that the intracellular RNA is almost decomposed onto non-flavoring ingredients with the RNA-decomposing enzymes contained in yeast cells.

When the autolysis of yeast cells is performed at a pH ranging from 6.0 to 6.6, both the yield of solid matter and GMP-forming ratio are high, therefore, the autolysis of yeast cells is preferably carried out at a pH ranging from 6.0 to 6.6.

In this pH range, when the phenomenon is more closely observed, it is found that the yield of solid matter drops gradually but on the contrary, the GMP-forming ratio becomes higher as the pH raises from 6.0 to 6.6. Therefore, the GMP content of a desired yeast extract may be controlled by selecting the pH at which the autolysis is performed.

When the autolysis of yeast cells is carried out at a pH above 6.6, the yield of solid matter is too low for the process to be performed economically.

After the extraction of RNA, an insoluble residue which is mainly cell walls of yeast included in the heated suspension may be removed by an entirely conventional method such as centrifugation and filtration. The time of removing the insoluble residue may be after either step (2) of extraction of RNA, or step (3) of hydrolysing RNA into 5'-nucleotides with 5'-phosphodiesterase. The third characteristics of the method of the present invention, resides in step (4) of forming flavoring 5'-nucleotide in the autolyzate solution or suspension by hydrolysing the extracted RNA into 5'-nucleotides with 5'-phosphodiesterase and by converting AMP into IMP with AMP deaminase if desired.

5'-phosphodiesterases employed according to the present invention are those which are capable of hydrolysing RNA into 5'-nucleotides containing GMP and AMP. For example, a 5'-phosphodiesterase derived from microorganisms belonging to genera of Aspergillus and Penicillium, or from malt or malt roots is employed. Among these, the enzyme derived from malt roots is preferably employed since it can be easily available from commercial and cheap malt roots and is capable of hydrolysing RNA effectively, and additionally, there is no doubt about safety of the enzyme. For use in the present invention, commercial malt roots are broken into small pieces, immersed in water to extract the enzyme, and the clear filtrate is then heated at a temperature of 60° to 65° C. for 5 to 10 minutes in order to inactivate a harmful enzyme which decomposes a resulting 5'-nucleotide into 5'-nucleoside and bases.

When 5'-phosphodiesterase derived from malt roots is employed, it is necessary to avoid using phosphate ions in autolysis process as buffering agent since the enzyme activity is completely inhibited in the presence of $4 \times 10^{-2}$ M phosphate ion.

And it is also preferable to refrain from addition of lactic acid before the RNA hydrolysis process since lactic acid which is usually employed for the purpose of improving a quality of yeast extract also inhibits the enzyme activity.

For hydrolysis of RNA, the quantity of malt roots necessary for hydrolysing RNA as an enzyme source is 10 to 30% by weight relative to the weight of the heated autolysate solution.

The hydrolysis of the RNA is usually carried out at a neutral pH and a temperature of 50° to 60° C. for 2 to 20 hours. Thereby, the extracted RNA is hydrolysed to 5'-nucleotides containing GMP and AMP. The resulting AMP may, if desired, be converted with AMP deaminase into flavoring IMP and for this purpose, any of variety of known AMP deaminases may be employed.

Among known AMP deaminases, the enzyme derived from fungus belonging to a yellow koji mold such as Aspergillus oryzae and Aspergillus sojae is preferably used, since both the enzyme and the fungus producing the enzyme are safe when used in food.

For use in the present invention, an AMP deaminase is prepared by the conventional method of culturing these fungi in a common nutrient culture medium.

A water extract of solid culture medium of the yellow koji mold or a crude enzyme preparation obtained by an entirely conventional method such as a salting out method using $(NH_4)_2SO_4$ or $Na_2SO_4$ is preferably used.

A commercially available enzyme prreparation for medical use such as Takadiastase is also preferably employed as a crude AMP deaminase.

For converting AMP into IMP, a quantity of a crude enzyme is 0.05 to 0.2% by weight of crude protein to using yeast cells on a dry basis.

An enzyme reaction for converting an AMP into IMP is usually carried out at a pH near the optimum pH of using enzyme and at a temperature ranging from 30° to 55° C. for 2 to 10 hours. The time of the enzymation can be reduced by conducting the enzymation along with that for hydrolysing RNA to 5'-nucleotides. After the enzymation, the enzymation mixture is preferably heated at a temperature of 90° to 100° C. for from 5 to 10 minutes in order to inactivate the enzyme activities. Then, a clear yeast extract containing flavoring 5'-nucleotide is obtained by separating insoluble residue.

The yeast extract obtained may be added as a solution to various foods and beverages. It may be also employed as pastes with a water content of 30 to 60% which is prepared by concentrating the clean yeast extract under reduced pressure or by using an osmotic membrane, or in the form of powders or granules prepared by conventional method such as spray-drying.

Having generally described this invention, a further understanding can be obtained by reference to certain specific examples which are provided herein for purpose of illustration only and are not intended to be limiting unless otherwise specified.

EXAMPLE 1

50 liter nutrient medium containing 5% glucose, 1% ammonium sulfate, 0.3% $KH_2PO_4$, 0.1% $MgSO_4.7H_2O$, 0.05% $CaCl_2.2H_2O$, 0.1% corn steep liquor of pH 5.5, was put into a 70 liter jar fermenter, and sterilized at 110° C. for 15 minutes, following which 200 ml of a seed culture broth of bakers yeast (Saccharomyces cerevisiae CBS 1523) cultured with aerobic shaking in the same culture medium at 30° C. for 18 hours, was inoculated, and cultured aerobically at 30° C. for 20 hours with vigorous aeration (⅓ V.V.M) and stirring at 500 r.p.m., under the pressure of 0.5 kg/cm².

After the cultivation, 2.75 kg of yeast cells in a form of cake with water content of 60% was obtained by centrifugation. The cake was then washed with water and water was added to the cake to prepare 8.0 liter of a suspension of yeast cells.

The suspension was mixed with 150 ml ethyl acetate and mixed well by stirring. Then, the suspension was divided into 1.0 liter suspension and the pH of the divided suspension were adjusted to from 5.5 to 7.5 as shown in table 1 with 30% NaOH. Each suspension was allowed to stand at 45° C. for 18 hours and each pH was controlled with alkali during the autolysis.

After the autolysis each autolysate suspensions was heated at 90° C. for 2.0 hours, thereby, the remaining enzymes were inactivated and remaining RNA was extracted.

On the other hand, to 20 kg of a commercial malt roots 20 liter water was added and the mixture was ground. Then, a clear extract obtained by removing the residue by filtration, was heated to 63° C. for 5 minutes in order to inactivate 5'-nucleotidase to obtain a crude enzyme solution for use of hydrolysing RNA.

To each heated suspension previously prepared, 200 ml of the crude enzyme solution was added and after the pH of each suspension was adjusted to 6.0, the enzymation reaction was conducted at 60° C. for 5 hours. After the enzymation, each enzymation mixture was heated to 90° C. for 5 minutes, and clear extract was obtained by removing the insoluble residue by centrifugation and dried under reduced pressure to prepare yeast extract in the form of powder. Each yield of solid matter and 5'-GMP forming ratio (GMP contained in yeast extract/GMP contained in the original yeast cells ratio in percentages) were measured and the result was shown in Table 1.

TABLE 1

The effect of pH on yield of solid matter and GMP forming ratio

| pH of autolysis | yield of solid matter (%) | GMP forming ratio (%) | GMP content in the extract (%) |
| --- | --- | --- | --- |
| 5.5 | 61 | — | — |
| 5.8 | 65 | 4.2 | 0.17 |
| 6.0 | 65 | 10 | 0.41 |
| 6.2 | 64 | 18 | 0.75 |
| 6.4 | 57 | 25 | 1.17 |
| 6.6 | 41 | 30 | 1.95 |
| 7.0 | 25 | 21 | 2.67 |
| 7.5 | 15 | 20 | 3.55 |

In Table 1, RNA content of yeast cells was determined according to the Schmidt-Thannhauser & Schneider method, and GMP content in RNA of yeast cells is calculated supposed that the four kinds of bases (guanine, adenine, uracil and cytosine) are contained equally.

The GMP in the yeast extract obtained was determined by liquid column chromatography using column of a cathion-exchanging ragin (LSZIZ). For the measurement, the eluting agent (pH of 2.6, $H_3PO_4$-NaOH buffer solution) was flowed through the column (4 mm$\phi \times$ 500 mm) at a flow rate of 0.6 ml./min. at 40° C. As shown in Table 1, both the yield of solid matter and the GMP-forming ratio are high when the autolysis are performed at a pH ranging from 6.0 to 6.6. It was found from the result of organoleptic test performed by a panel of 20 members who had been specially trained for this kind of test that the yeast extract, obtained by autolysis at pH 6.0 to 6.6, especially obtained at pH 6.2 to 6.4 has less of an unfavorable odors peculiar to yeast itself and has a thickness or body in taste which resemble that of beef extract, and that the quality of the yeast extract is excellent owing to its strong flavoring taste.

EXAMPLE 2

1.0 liter suspension of yeast cells prepared in the same manner as described in Example 1 was mixed with 30 ml ethyl acetate and the autolysis of the yeast cells was carried out at pH 6.2 and 52° C. for 20 hours with mild stirring, during which the pH of the suspension was controlled nearby 6.2 with alkali. After the autolysis, the autolysate suspension was heated at 92° C. for 2.0 hours, thereby the undesirable enzymes were inactivated and a remaining intracellular RNA was extracted. From the heated solution, clear extract solution was obtained by centrifugation and the solution used to wash the residue was added to the clear solution to obtain 1 liter yeast extract. On the other hand, two kinds of crude enzyme preparation was prepared according to an entirely conventional method.

First, each 50 ml culture medium containing 5% glucose, 0.5% peptone, 0.1% $KH_2PO_4$, 0.04% $MgSO_4.7H_2O$, 0.04% $CaCl_2$ and 0.1% phytin, of pH 7.0 was put into a 500 ml shaking flask, and heated at 120° C. for 10 minutes for sterilization. After each medium was cooled, 1.5 ml ethanol was added and Penicillium citrinum IAM 1131, grown on potato dextrose agar slant was inoculated into the culture medium and cultured with aerobic shaking at 30° C. for 3 days. After the cultivation, a clear culture filtrate was heated at 60° C. for 15 minutes in order to inactivate harmful 5'-nucleotidase to obtain a 250 ml crude enzyme solution.

For preparation of AMP deaminase, Aspergillus oryzae ATCC 14578, grown on potato dextrose agar slant, was inoculated into each 50 ml of sterilized culture medium containing 5% glucose, 0.5% $KH_2PO_4$, 0.1% $MgSO_4.7H_2O$, and 0.05% corn steep liquor, of which pH is 6.0, and cultured with shaking at 30° C. for 2 days. To the clear filtrate, solid ammonium sulfate was added and a crude enzyme precipitated by 80% saturation with ammonium sulfate was collected by filtration, washed with ethanol-water solution (ethanol: water=2:1) and dried under reduced pressure to obtain 0.2 g crude enzyme preparation.

To 1.0 liter yeast extract previously prepared, 250 ml of the crude enzyme solution derived from Penicillium citrinum was added and the mixture solution, after the pH was adjusted to 4.5, was allowed to stand at 70° C. for 2 hours in order to hydrolyse the extracted RNA to 5'-nucleotides. After the enzymation, the pH of the solution was adjusted to 6.0 with alkali with 0.2 g crude enzyme of AMP deaminase was added and an enzymation was carried out at 45° C. for 3 hours. Then solution was heated at 95° C. for 10 minutes, and evaporated under reduced pressure to obtain 86 g yeast extract. The resulting yeast extract contained 0.78% 5'-GMP and 0.7% 5'-IMP respectively and had a strong flavoring taste.

EXAMPLE 3

Pichia farinosa CBS 2006, grown on potato dextrose agar slant, was inoculated into a culture medium containing 0.5% ammonium acetate, 1% corn steep liquor, 0.2% $KH_2PO_4$, 0.5% ammonium sulfate, 0.1% $MgSO_4.7H_2O$ and cultivation was carried out at 30° C. and at ph 6.0. The pH was maintained at 6.0 by adding a mixture of acetic acid and ammonium acetate during the cultivation. The cultivation was stopped when maximum growth was attained, and yeast cells were harvested by centrifugation. After washing with water, 1.0 liter yeast cream with water content of 85% was obtained and allowed to stand at 45° C. for 20 hours for autolysis. The pH of the cream was maintained at 6.6 with 30% NaOH during the autolysis. Then, 50 g yeast extract with water content of 5% was prepared in the same manner as described in Example 1. The yeast extract thus obtained contained 1.4% 5'-GMP and has a strong flavoring taste.

What is claimed is:

1. A method for producing a yeast extract containing flavoring 5'-nucleotide and having an improved thickness or body in taste which comprises:

(1) autolysing suspended yeast cells in the absence of added enzymes and added sodium chloride, and in the presence of an organic material that stimulates autolysis at a constant pH ranging from 6.0 to 6.6, then (2) heating the autolysed suspension at a temperature of 90° to 100° C. for 1 to 3 hours in the absence of added sodium chloride thereby extracting intracellular ribonucleic acid; and thereafter performing the following steps in any order;

(3) hydrolysing the extracted ribonucleic acid with a 5'-phosphodiesterase to form nucleotides including adenosine monophosphate and;

(4) separating the resulting extract from the insoluble residue.

2. The method of claim 1 wherein step (2) is followed by steps (3) and (4) in consecutive order.

3. The method of claim 1 wherein step (2) is followed by steps (4) and (3) in consecutive order.

4. The method of claim 1 wherein said 5'-phosphodiesterase is that derived from malts or malt roots.

5. The method of claim 1 wherein said step (3) further comprises converting adenosine monophosphate to inosine monophosphate by means of a deaminase enzyme.

* * * * *